United States Patent

Hazen

[11] Patent Number: 5,451,498
[45] Date of Patent: Sep. 19, 1995

[54] DENTURE COVERING EXISTING TEETH AND GUMS

[76] Inventor: Anthony P. Hazen, 4010 E. 53 St., Tulsa, Okla. 74135-4816

[21] Appl. No.: 228,898

[22] Filed: Jun. 23, 1994

Related U.S. Application Data

[63] Continuation of Ser. No. 897,762, Jun. 12, 1992, Pat. No. 5,324,198.

[51] Int. Cl.⁶ .................. A61C 13/00; A61C 13/08
[52] U.S. Cl. ........................................ 433/171; 433/167
[58] Field of Search ............... 433/167, 171, 172, 215

[56] References Cited

U.S. PATENT DOCUMENTS

| 277,933 | 5/1883 | Richmond | 433/172 |
| 973,343 | 10/1910 | Corcoran | 433/172 |
| 3,716,918 | 9/1971 | Tole et al. | 433/172 |
| 4,580,980 | 4/1986 | Acquanetta | 433/167 |
| 4,764,115 | 8/1988 | Willits et al. | 433/177 |
| 5,018,533 | 5/1991 | Hawkins | 128/848 |

Primary Examiner—Nicholas D. Lucchesi

[57] ABSTRACT

This device includes two separate impression-molded all gum and cap-cup encasements (upper and lower arches) with veneered artificial teeth mounted to the encasement walls. The veneered encasements comprise the completed all gum and cap-cup dental device. The completed cap-cup encasements cover the upper and lower arches of full sets of natural teeth and gums.

1 Claim, 2 Drawing Sheets

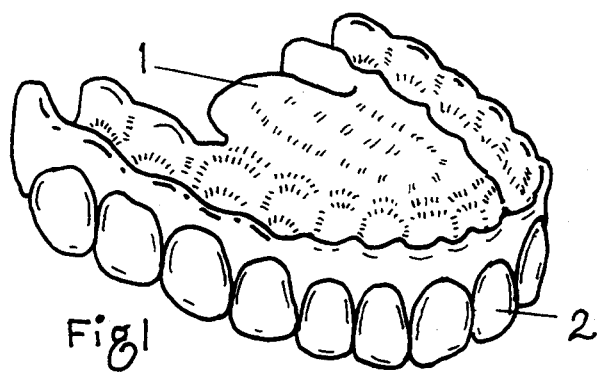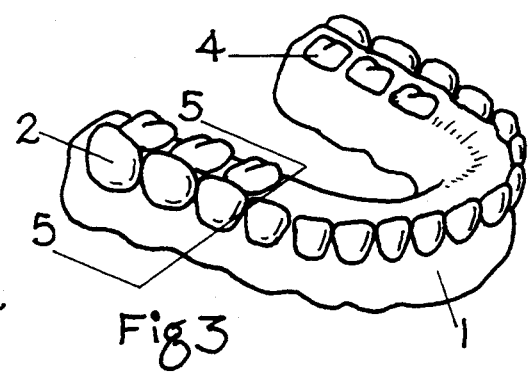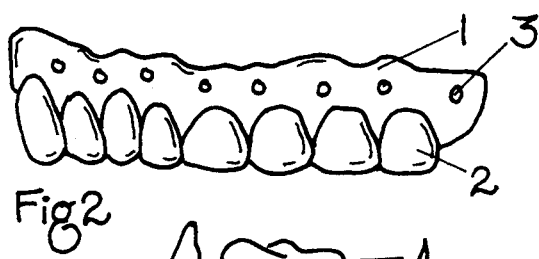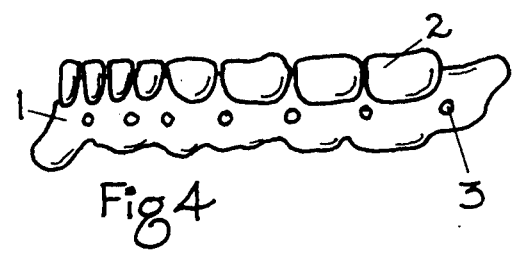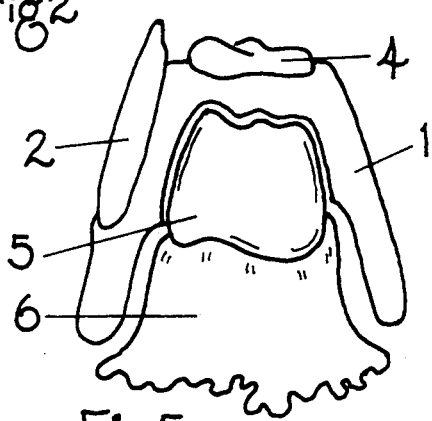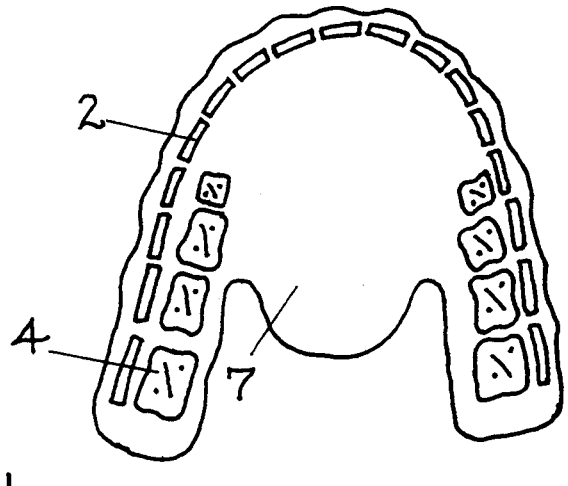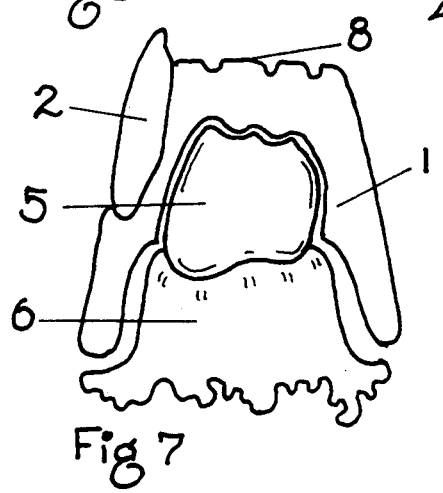

DENTURE COVERING EXISTING TEETH AND GUMS

This application is a continuation of application Ser. No. 07/897,762, filed Jun. 12, 1992, now U.S. Pat. No. 5,324,198.

BACKGROUND OF THE INVENTION

The present invention relates to prosthetic denture devices. However, its application and relative functional use differs. Denture devices provide teeth where there are none, but should be in direct position and proportion to the underlying vacated gum.

This device goes over existing teeth and gums, and bridges over missing teeth where possible.

The present invention relates to prosthetic dental caps and/or crowns. However, the application and relative functional use of this invention differs. Caps and/or crowns are permanently affixed to the teeth. This device is not permanently affixed to the teeth.

In design appearance this device differs from caps and/or crowns in that it is one whole unit rather than multiple units, as used in caps and/or crowns.

SUMMARY OF THE INVENTION

It is the object of this invention to cover whole sets of human teeth, palate and gums (upper and/or lower arch devices) in an aesthetically pleasing skeletal-dental prosthetic device constructed from all types of approved prosthetic dental materials, i.e., acrylics, plastics, vinyl, hard and soft rubbers, metals, silicone, gold and/or combinations thereof.

It is the intention of this device, when properly used and prescribed, to produce superior functional and oral hygiene which will result in extended life to the teeth.

It is also the intention of this device to supply the cosmetic dental industry-with a new and unique method and dimension in aesthetically pleasing artificial teeth and gums. The result is happy users with a new design in teeth never available to them before now.

DESCRIPTION OF THE PREFERRED EMBODIMENT

The dental device includes an all-gum tooth cap-cup encasement (1) constructed from dental material which artificial veneer teeth (2) are joined or mounted to the wall of the encasement cup. The encasement cup is perforated with periodic circulation holes (3). The gum and teeth encasement is created from an impression-mold of the user's teeth and gums.

The device may be constructed from all approved prosthetic dental materials and combinations thereof, i.e., acrylics, plastics, silicone, vinyls, hard and soft rubbers, metals and gold. The variations of the construction design and use of these materials are determined by the dentist according to the user's needs.

Some other possible construction design and material variations are represented in FIGS. 2 through 7.

List of elements:
1. encasement
2. side veneers
3. circulation holes
4. bottom veneers
5. tooth
6. gum
7. palate
8. molded plastic surface without bottom veneer
9. cast metal bottom
10. plastic encasement
11. brace band
12. plastic fill
13. all metal encasement

BRIEF DESCRIPTION OF THE DRAWINGS

FIG. 1 is a perspective view of a dental device for the upper arch.

FIG. 2 is a side view of the dental device for the upper arch of FIG. 1.

FIG. 3 is a perspective view of a dental device for the lower arch.

FIG. 4 is a side view of the dental device for the lower arch of FIG. 3.

FIG. 5 is a section view along the line 5—5 of FIG. 3.

FIG. 6 is a bottom view of FIG. 1.

FIG. 7 is a section view of an alternative embodiment without bottom veneers.

Figure 8:
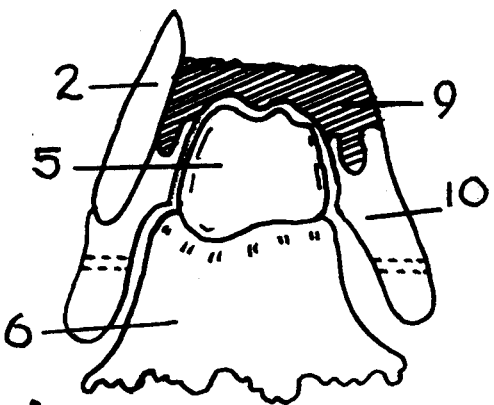
FIG. 8 is a section view of an alternative embodiment having a cast metal bottom and plastic encasement.
Figure 9:
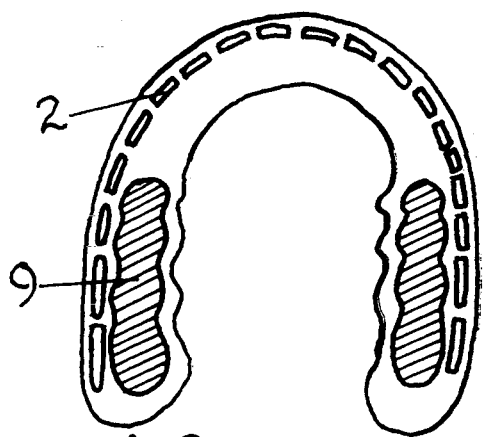
FIG. 9 is a bottom view of a lower arch of FIG. 8.
Figure 10:
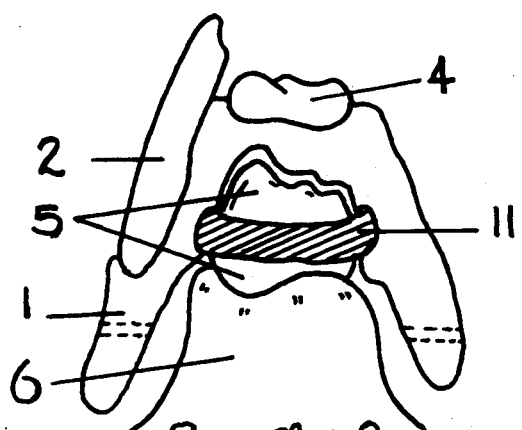
FIG. 10 is a section view of an alternative embodiment having brace bands.
Figure 11:
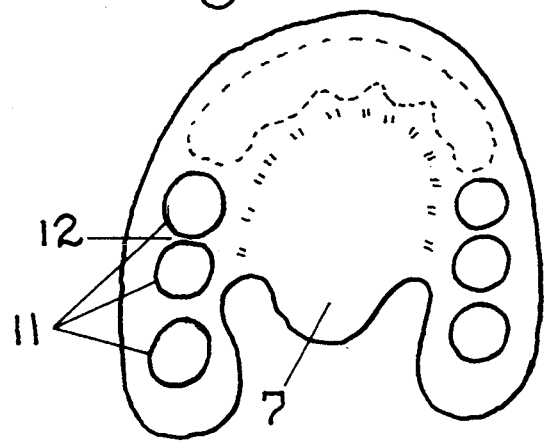
FIG. 11 is a bottom view of the upper arch of FIG. 10.
Figure 12:
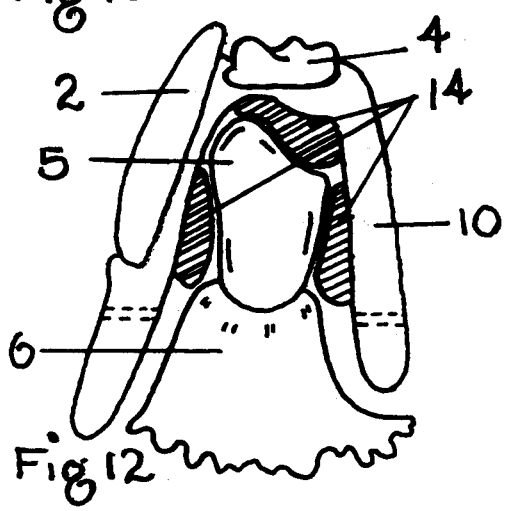
FIG. 12 is a section view of an alternative embodiment with a co-soft liner.
Figure 13:
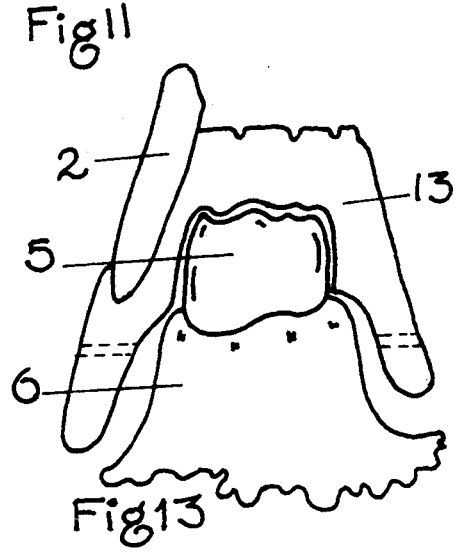
FIG. 13 is a section view of an alternative embodiment with a metal encasement.

I claim:

1. A method for enhancing the facial appearance by providing aesthetically pleasing artificial teeth for non-denture wearers, for bridging spaces left by missing teeth, for protecting damaged or hypersensitive teeth from temperature extremes, and for strengthening the user's ability to more effectively masticate food, comprising the steps of;

forming an encasement constructed from approved dental materials, said encasement corresponding to an impression mold of the user's natural teeth and gums, said encasement having inner encasement walls which conform to the user's natural teeth and gums and outer encasement walls, mounting on said outer encasement walls a plurality of artificial teeth ground down to veneers.

* * * * *